United States Patent [19]

Andersson et al.

[11] Patent Number: 5,607,305
[45] Date of Patent: Mar. 4, 1997

[54] PROCESS AND DEVICE FOR PRODUCTION OF THREE-DIMENSIONAL DENTAL BODIES

[76] Inventors: Matts Andersson, Hammarströms Täppa 2, S-443 39 Lerum; Anders Törnquist, Molndalsvägen 7, S-142 63 Göteborg, both of Sweden

[21] Appl. No.: 271,444
[22] Filed: Jul. 7, 1994

[30] Foreign Application Priority Data

Jul. 12, 1993 [SE] Sweden .................................. 9302400

[51] Int. Cl.$^6$ ...................................... G01B 11/24
[52] U.S. Cl. .................... 433/223; 433/213; 364/474.05
[58] Field of Search .......................... 433/25, 27, 213, 433/214, 215, 223, 229; 364/474.05

[56] References Cited

U.S. PATENT DOCUMENTS

| | | | |
|---|---|---|---|
| 4,084,244 | 4/1978 | Floter | 364/474 |
| 4,394,608 | 7/1983 | Tryber et al. | 364/474 |
| 4,411,626 | 10/1983 | Becker | 433/223 |
| 4,575,805 | 3/1986 | Moermann et al. | 433/223 |
| 4,663,720 | 5/1987 | Duret et al. | 433/214 |
| 4,742,464 | 5/1988 | Duret et al. | 433/214 |
| 5,003,484 | 3/1991 | Vollmayr | 364/474.03 |
| 5,027,281 | 6/1991 | Rekow et al. | 364/474.05 |
| 5,092,022 | 3/1992 | Duret | 433/213 |
| 5,184,306 | 2/1993 | Erdman et al. | 364/474.03 |
| 5,193,282 | 3/1993 | Aramaki et al. | 364/474.03 |
| 5,204,824 | 4/1993 | Fujimaki | 364/474.03 |
| 5,219,282 | 6/1993 | Larin | 433/213 |
| 5,224,049 | 6/1993 | Mushabac | 433/223 |
| 5,313,400 | 5/1994 | Tsukamoto | 364/474.03 |

FOREIGN PATENT DOCUMENTS

90/15376  12/1990  WIPO .................................. 433/215

*Primary Examiner*—Edgar S. Burr
*Assistant Examiner*—Steven S. Kelley
*Attorney, Agent, or Firm*—Pollock, Vande Sande & Priddy

[57] ABSTRACT

A method for scanning, in connection with the production of a three-dimensional dental body, an outer contour of a rotating model with a scanning device which operates at a scanning angle relative to the rotational axis of the model, comprises mounting the model in or on a rotatable holder, supporting the model in the holder so that the contour to be scanned on the model above a preparation line is exposed to the angled scanning device, applying the scanning device towards a surface situated on the model below the preparation line, activating the holder for rotation and the scanning device for contour scanning, and activating during the contour scanning at least one of the scanning device and the holder for movement in the vertical direction of the model.

14 Claims, 3 Drawing Sheets

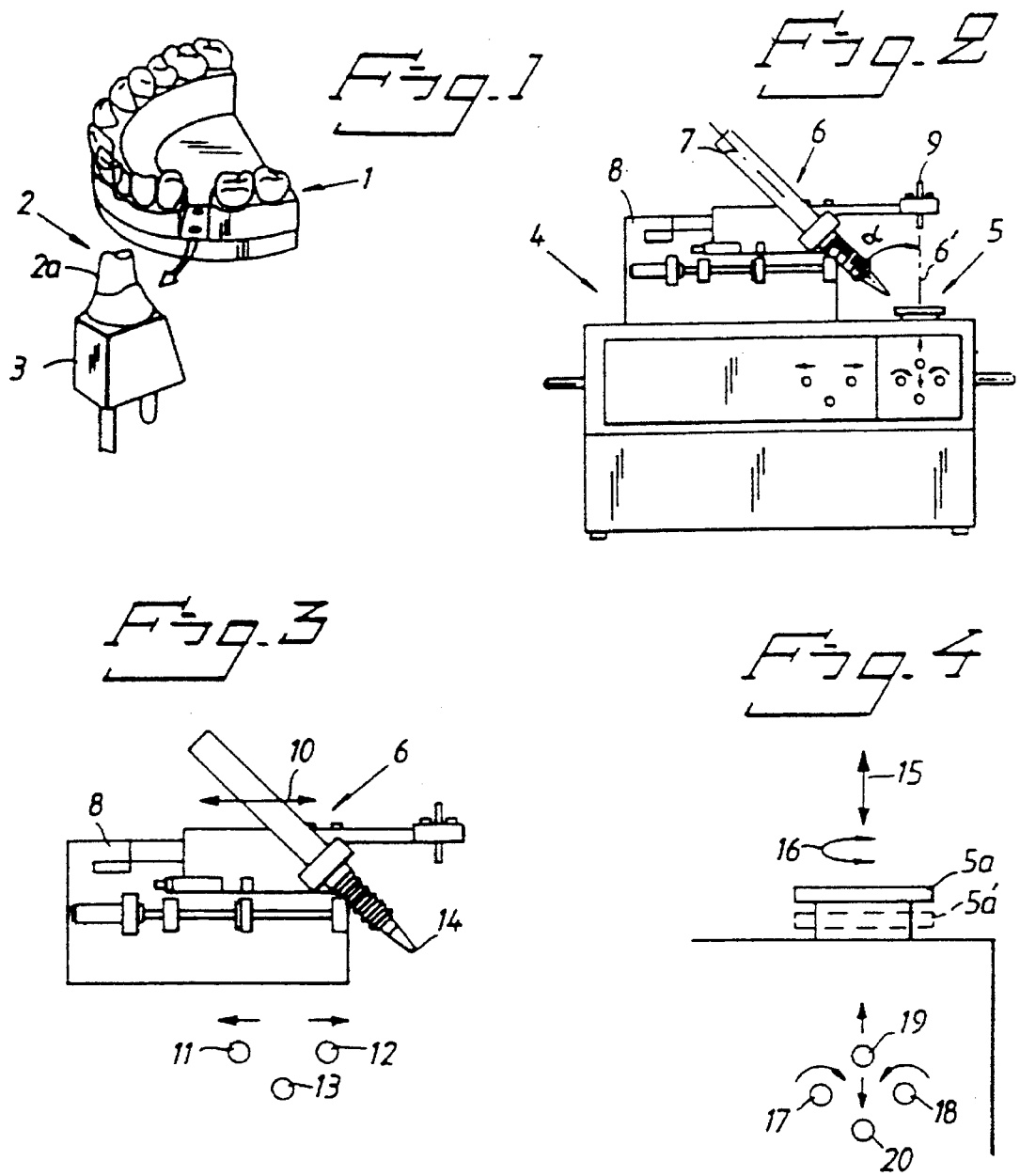

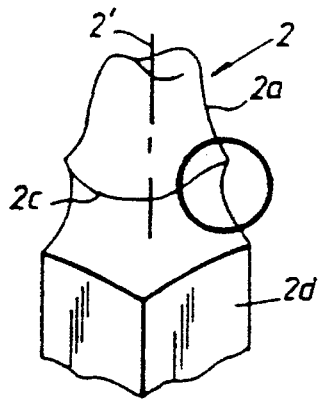
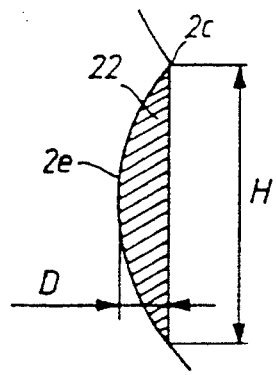
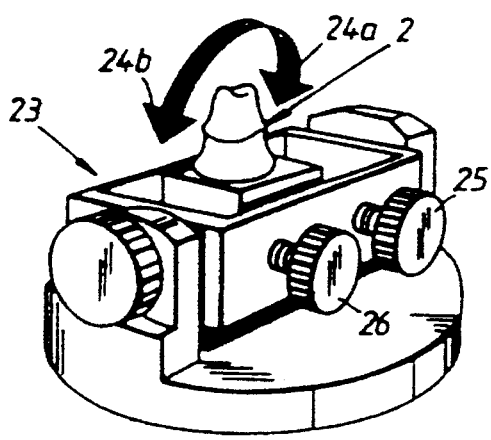
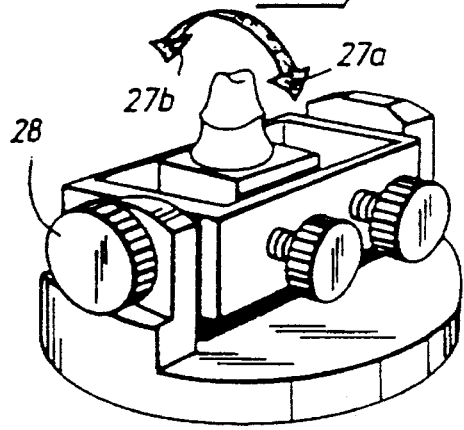
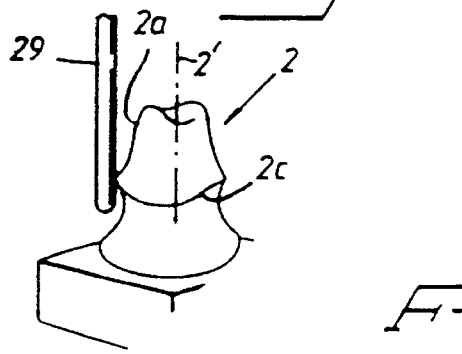
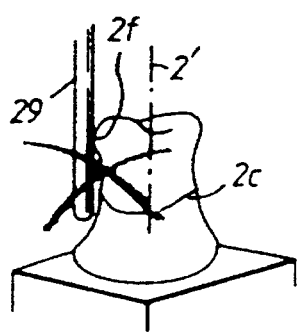

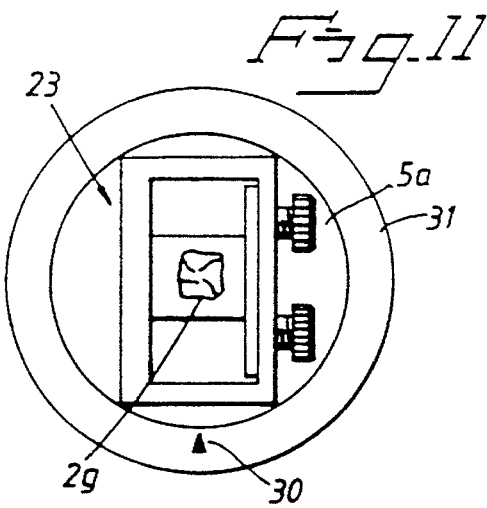
Fig. 11
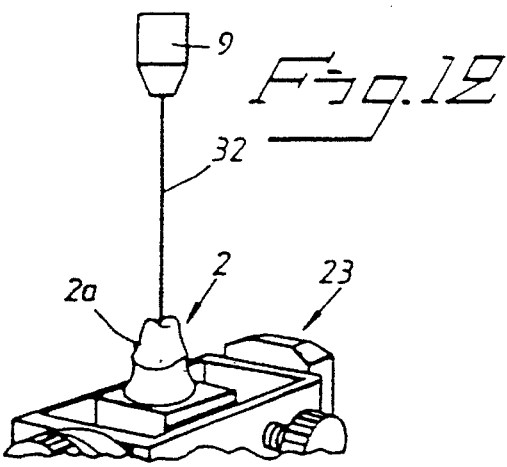
Fig. 12
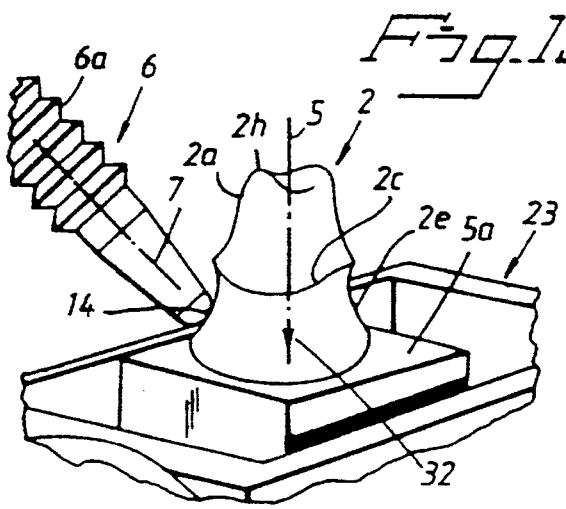
Fig. 13
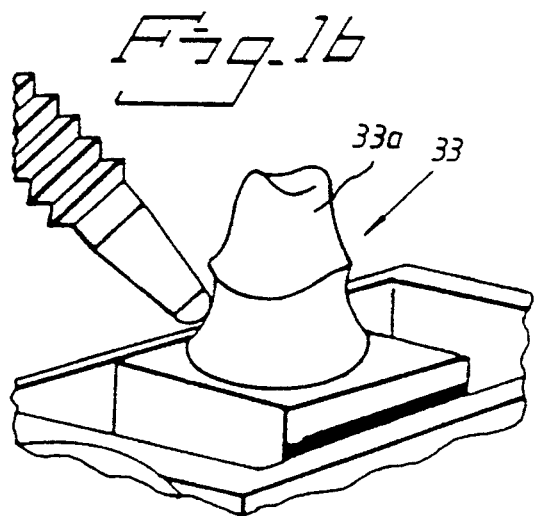
Fig. 16
Fig. 14
(ESC) Cancel    Data = 4231
1. Adjust the probe. Start position!
2. Check that the scanning key is on "ON"
3. Press (ENTER) to start reading.
Fig. 15
Operator    Patient ID    Tooth
[Anders]    [123456-7890] [34]
Order No.   Type of job
P.98.7654   ( ) Titanium
Priority    ( ) Ceramic
            (o) Titanium CAD
            ( ) Ceramic CAD
Remarks     ( ) Other
Dentist Matts Andersson

PROCESS AND DEVICE FOR PRODUCTION OF THREE-DIMENSIONAL DENTAL BODIES

FIELD OF THE INVENTION

The present invention relates to a process for scanning, in connection with the production of a tooth, bridge or similar product usable in the human body, an outer contour of a rotating model by means of a scanning device which operates at a scanning angle, for example 45°, relative to the rotational axis of the model. The invention also relates to a device for implementing the process.

BACKGROUND OF THE INVENTION

From Swedish patent 9003967-8 (468 198), it is known to carry out a scanning or reading function on a rotating model, in which a scanning device is set at an angle (45°) relative to the rotational axis of the model. The reading is utilized by a computer for the further processing of input data and production of the product in question, which is primarily a tooth, bridge or other dental three-dimensional body.

SUMMARY OF THE INVENTION

The entire production process of formulated or desired products must be executed such that a relatively very high manufacturing accuracy is accomplished, in connection with which it may be mentioned that in many cases an accuracy of 0.01–0.05 mm is required. This places high demands upon, among other things, the capacity of the reading function to be performed with great accuracy.

The reading should be performed by the average dental technician or dentist without the need to acquire over-extensive special skills in data-processing. The invention aims to solve these problems and proposes a tool which is easy to learn to use and implement together with normal tasks performed by the dental technician/dentist.

There is a requirement for the reading to be performed with necessary accuracy on the spot, entirely separate from the actual manufacture of the product. The dentist/dental technician should be able individually to perform a data-storage and data-transfer to the manufacturer. The invention solves this problem too.

The new tool should be operated on the basis of the principles, hitherto practiced regarding the formulation of the preparation model. The tooth preparation model should be separated from a plastic cast in a manner which is well known and then utilized in the reading function. The invention solves this problem and enables the dental technician/dentist to retain the model during its manufacture, whereby the model need not be physically sent away to a manufacturer.

The dentist or dental technician should be able to perform final adjustments to a produced crown or equivalent. The invention solves this problem by virtue of he or she being able to quickly perform, as an intermediate step, a production or manufacture of a product corresponding to the model.

The tool for the dental technician/dentist should involve the utilization of conventional data-processing equipment currently on the market and a reading function which is technically simple. The invention solves this problem and proposes a specially adapted reading apparatus which is easy to handle. In addition, the utilization of a conventional personal computer for example, an IBM-compatible PC of the 386 type or higher capacity) is made possible. The personal computer preferably comprises a built-in modem, by means of which read files can be transferred to the manufacturer via the public telecommunications/data network. The equipment is simple to connect.

The characteristic feature of a process according to the invention is that the model is mounted in a rotary holder and is supported by the holder such that the scanned contour, above a preparation line on the model, can be exposed throughout to the angled scanning device. The process is additionally characterized in that the scanning device is directed towards a surface situated on the model below the preparation line and that the holder is activated for rotation, and the scanning device is activated for contour scanning. During the contour scanning, the scanning device and/or the holder are moved in the vertical direction of the model.

In embodiments of the inventive concept, the model is installed in a fixture and adjusted in two mutually perpendicular directions located in the same plane, thereby enabling the model to be centered relative to the rotational axis of the holder. In addition, a member (parallel pin) can be utilized, which can be disposed parallel to the rotational axis and can be brought into interaction with the model material at the preparation line when the model assumes its position in the fixture. The position of the model in the fixture is in this respect such that the contour is placed or comes between the member and the rotational axis without negative recesses and reading shadows. The fixture is placed on the holder, for example a turntable, and centered using centering members. The contour is read preferably by means of a reading member exhibiting a spherical front surface (so-called probe), which is brought to bear against the surface located below the preparation line and against the contour.

The scanning member can be brought into physical contact with the surface below the preparation line. The physical contact remains until the scanning member, in its scanning function, has reached the upper part of the model, where the scanning member is assigned an action or a return movement Which results in the cessation of the interaction of the scanning member with the model contour. The holder or scanning member can be movable in the vertical direction of the rotational axis during the scanning function. When the scanning of the contour is completed, a respective unit which is movable in the vertical direction begins return movement to the starting position.

Both the model and a sleeve (cap) which can be fitted to the model can be scanned using the scanning device. The model can be scanned first and, thereafter, the sleeve fitted onto the model. In order to avoid disturbing the set values of the model, the sleeve can be fitted with great accuracy, utilizing glue or some other adhesive material. With the double reading, the inner surface (corresponding to the outer surface of the model) and outer surface of the sleeve are fixed and data-stored.

A device for implementing the process according to the present invention is characterized principally in that a holder is arranged to support the model such that the contour of the model above a preparation line on the model can be exposed throughout the reading or scanning with the angled scanning device. The scanning device can be adjusted, at the start of the scanning function, against a surface situated below the preparation line. The holder can be activated for rotation and the reading device can be activated for contour scanning. The scanning device and the holder are arranged to perform reciprocal movements in the vertical direction of the model during the scanning function.

In one embodiment of the inventive concept, the scanning device is assigned a return movement when the scanning device has completed its contour reading, which return movement results in the cessation of a physical interaction between the scanning device and the model. The scanning device and holder respectively, can likewise be assigned a return movement when the contour scanning is completed.

In accordance with the inventive concept, the preparation model which can be read using the scanning device should be configured with a clearly marked preparation line or preparation boundary, below which there is preferably configured an indentation of no less than about 1 mm in height, calculated in the vertical direction of the model, and having a depth no greater than about ½ mm.

The above described inventive tool is easy to handle for the dental technician and dentist. The equipment is computer-based. Despite the fact that this is a relatively new technique within dental technology, the above-mentioned proposals mean that the equipment can normally be incorporated into the ordinary working tasks of the dental technician and dentist, respectively, in connection with the provision of replacement dentures. The high level of accuracy which is sought can be satisfied throughout the production system for the particular product. The reading function can be performed separately from the rest of the production and can result in the delivery of the data-values to the manufacturer. Standardized products as regards computer equipment, modem, and the like can be utilized in this context.

BRIEF DESCRIPTION OF THE DRAWINGS

A presently proposed embodiment of a process and a device exhibiting the characteristics which are indicative of the invention will be described below with simultaneous reference to the appended drawings, in which:

FIG. 1 shows a casting, for example in plastic, of a jaw with teeth and a preparation model taken from this, in perspective section from above, FIG. 2 shows a scanning device from the side, FIG. 3 shows an enlarged view of parts of the device according to FIG. 2, FIG. 4 shows parts of the scanning device according to FIG. 2, from the side, FIG. 5 shows a personal computer unit which can be used together with the scanning device according to FIG. 2, in perspective section from above, FIG. 6 shows the embodiment of the preparation model according to FIG. 1, in perspective section from above and enlarged, FIG. 7 shows parts of the preparation model according to FIG. 6, in longitudinal section, FIG. 8 shows, in greater detail, a fixture for the preparation model, which can be applied to the holder, in perspective section from above, FIG. 9 shows the fixture according to FIG. 8 as it is adjusted in a direction which is essentially perpendicular to the direction indicated in FIG. 8, FIGS. 10–10a show preparation models which are usable and non-usable, respectively, in connection with the rest of the equipment, in perspective section from above, FIG. 11 shows the fixture according to FIGS. 8 and 9 applied to the holder, in horizontal view, FIG. 12 shows centering of the fixture and preparation model on the holder, in perspective view, FIG. 13 shows an interaction between the scanning device and the preparation model mounted in the holder, FIGS. 14–15 show menus on computer screens in connection with the scanning process, and FIG. 16 shows the interaction of the scanning device with the model, in which a sleeve (cap) is applied to the model, in perspective section from above.

DETAILED DESCRIPTION OF THE PREFERRED EMBODIMENT

In FIG. 1, a conventional casting of a human jaw is indicated by 1. From the casting 1 there is extracted, in a known manner, a preparation model 2, whose contour 2a is to be read. The model is disposed on a holding part 3. The casting 1 can be made in plastic, plaster, and the like.

FIG. 2 shows a scanner 4 which is provided with a holder 5 and a scanning device 6. The holder is disposed rotatably around a rotational axis 6', and the longitudinal axis 7 of the scanning device is inclined with respect to the rotational axis 6' at an angle alpha. The angle is, in one embodiment, preferably 45°. The scanning device exhibits a longitudinally displaceable slide 8, in which the scanning device 6 is disposed. The slide is displaceable relative to the holder 5, which can be raised and lowered in the direction of the rotational axis 6'. The slide exhibits a centering part 9, which is described in greater detail below. The slide 8 is shown in FIG. 3, in which the movement direction of the slide is indicated by 10. The device includes actuating keys 11 and 12 for the movement directions of the slide and switch-on members 13 by which the scanning function can be switched on and off. The scanning device 6 comprises a front part 14 having a spherical front surface, as described below. The scanning unit has, in one embodiment, a rod-shaped configuration and operates with a scanning function based on known principles. The scanning function can be monitored on a visual display unit, as described below.

FIG. 4 shows the holder in enlarged views relative to FIG. 2. The movement directions of the holder 5 are indicated by 15 and the rotary directions of the holder 5 by 16. The holder exhibits a bearing surface 5a which, in the figure, is shown in two positions, one of which is shown by continuous lines, while the other position is shown by dashed lines 5a'. The scanning device exhibits actuating keys, which can be manually operated like the keys 11, 12 and 13. The actuating members for the holder are indicated by 17, 18, 19 and 20. The actuating members 17 and 18 are utilized to adjust the rotary movement of the holder in accordance with what is stated below, while the actuating members 19 and 20 provide for raising and lowering movements 15, respectively, for the holder.

FIG. 5 shows an example of a personal computer which can be used in the and which can be, for example an IBM-compatible PC comprising a processor of the 386 type or of a more powerful type. The computer can operate on a DOS 5.0 operating system or higher. The computer can comprise an internal modem and operates with at least two megabytes (MB). The personal computer can be equipped, in a known manner, with "mouse" function, color screen and can exhibit an extra I/O card. The modem can be of the telephone modem type, and a Hayes-compatible modem can be used, for example. As the communications program, a COMMUT 2.0 program from Central Point can be utilized with included software. Where scanned data is not sent by modem via a telecommunications network, the data can be sent on data files on diskette, by post or by courier.

FIGS. 6 and 7 show preferred embodiments of the preparation model 2. The preparation model 2 should thus exhibit a clearly marked preparation line or preparation boundary 2c. The contour 2a must not exhibit any recesses or negative angles above the line 2c. The model 2 should exhibit a parallel base 2d, so that the model can be fixed in a deployed fixture, as described below. The contour should also have a shaping to prevent "shadows" being formed for the scanning member (see 14 in FIG. 3) when this operates at a fixed angle, for example, 45°. It is also advantageous to dispose below the preparation line 2c a recess or depression, which is symbolized by the recess surface 2e. The recess should preferably have a height H of at least 1 mm and a depth D of 0.5 mm or less. The shaded portion 22 in FIG. 7 shows the shaping of the recess.

FIGS. 8–9 show the installation of the preparation model 2 in or on a fixture 23, which can be applied, in turn, to the holder 5. The fixture can be configured, in a known manner, with holding members for the part 2d according to FIG. 6. The fixture is in this case arranged to be able to angle-adjust the model in the directions of the arrows 24a and 24b, the tilting in the direction of the arrow 24a being managed by a manual maneuvering member 25 and the tilting in the direction of the arrow 24b being managed by a manual member 26. The model can also be tilted, in accordance with FIG. 9, in directions 27 and 27b perpendicular to the directions 24a and 24b, which directions 27 and 27b are achieved with the aid of a manual maneuvering member 28. In accordance with the figures shown, the model can be considered to have a cardan suspension in the fixture. The model is disposed in the fixture such that no recesses and preferably no scanning shadows are formed above the preparation line. The fixture permits adjustment, according to the above, in the longitudinal and transverse directions.

In accordance with FIGS. 10 and 10a, a parallelometer pin 29 can be utilized. The parallelometer pin 29 is placed parallel to the rotational axis 6' of the preparation model 2. FIG. 10 shows that the contour 2a terminates upwards/inwards as viewed from the preparation line 2c. In FIG. 10, the pin 29 therefore bears against the material at the preparation line and all the rest of the material above the preparation line is situated between the pin 29 and the rotational axis 6'. This is not the case according to FIG. 10a, which shows that the pin bears against model material 2f situated above the preparation line 2c and cannot, for this reason, be accepted.

According to FIGS. 11 and 12, the fixture 23 is thereafter applied to the holder 5a. The fixture is in this case installed such that a curved surface 2g of the model is directed towards a marking 30 on a ring 31 surrounding the turntable or holder 5a. The model is centered accurately with the aid of the said centering part 9 (see FIG. 2) and a plumbline 32 disposed in the part 9 and extending down towards the model 2.

According to FIG. 13, the contour scanning is initiated by the scanning device being brought into physical contact with the model 2 via its spherical front surface 14. The bearing contact takes place against the surface 2e below the preparation line 2c. The surface 14 performs movements in the direction of the longitudinal axis 7 as the contour is scanned. A bellows-shaped part which protects the scanning function is indicated by 6a. The scanning proceeds in the present case in such a way that the holder 5a is lowered downwards in the direction of the arrow 32 as the scanning takes place. When the spherical surface has scanned the whole contour 2a and reached the top 2h of the model, the scanning device 6 is assigned a return movement in the direction of the longitudinal axis 7, where the contact with the model ceases and the latter is exposed to pickup vis-a-vis the scanning device. Following completion of the scanning, the holder 5a returns to its vertical position shown in FIG. 13.

The process according to the present invention comprises an adjustment position of the scanning device as a starting position. In FIG. 13, this means that the spherical surface 14 (probe) is adjusted as far as it will go to the right in the figure. The height of the holder or turning part 5 is vertically adjusted such that the front part of the scanning member rests against the model, approximately 1 mm below the preparation line 2c. For this adjustment, the maneuvering members 11 and 12 or 17, 18 and 19, 20, respectively, can be utilized. It is advisable to avoid sudden activation movements which result in the probe hitting hard against the preparation model. The adjustment phase also includes the requirement that the spherical surface 14 should be situated below the preparation line around the whole of the model. A check of this kind can be made by rotating the model with the aid of the said maneuvering members.

The scanning procedure can thereafter be started, and the start is effected by activation of the maneuvering member 13. On the visual display unit, the "start scanning" mode can thereafter be activated, for example by actuating the activation key, the "ENTER"-key, on the computer terminal. The computer and its program thereafter manage the scanning procedure, and the turntable/holder 5a is rotated and vertically displaced according to a pattern which is determined using the program. The measuring probe systematically scans the surface of the preparation model 2 until it has reached a point above the model, where it stops. When the scanning is completed, the probe automatically performs the return movement and the table regains its starting height.

FIG. 14 shows a menu on the computer screen. The menu comprises an item 1, at which the probe should be set in the starting position according to the above. According to item 2, a check is made to establish that the scanning key 13 is in the "on" position. According to item 3, "ENTER" is actuated on the computer terminal, whereupon a reading is started automatically. The program in the computer delivers or provokes control signals controlling the rotation and vertical movement (that is lowering) of the holder.

The reading by means of the scanning device and the simultaneously rotating and lowering holder/turntable is performed with respect to the contour of the model. Read data is input, in a known manner, into a particular file for subsequent use.

FIG. 15 shows an additional menu/form on which the person/dental technician can enter various information relating to the scanned tooth. "Type of transfer" can be included here. It is also possible to enter the type of copied material and whether the shape has been determined from a scanned sleeve (either titanium or ceramic) or whether it has subsequently been processed in the computer. The name of the dentist and other data can be entered, such as order number, priority, patient identification, tooth type, and the like. A space for remarks can additionally be included. The computer is then activated for "save data file" and the scanning is complete. Information or data which have been scanned and stored in the computer can be transferred, according to the above, to the manufacturer.

FIG. 16 shows a scanning function for a sleeve 33 (cap). The inner contour of the sleeve 33 is scanned in accordance with the above, that is the outer contour of the preparation model 2 corresponds to the inner contour of the sleeve 33. This scanning is carried out according to the above. The sleeve 33 is thereafter applied to the model and care should be taken in this respect to ensure that adjustments which have been made for the model are not affected. The sleeve can be glued to the model. The system coordinates the two scannings of the inner and outer surfaces by using the same system of coordinates. This means, for example, that the starting position for the scanning device relative to the model must be the same, that is the scanning device must be applied to that same point or position which was utilized when only the model was scanned. Once the sleeve has been fixed on the model, the procedure according to the above can be repeated for scanning of the outer contour of the sleeve. The difference is, however, that a difference emerges in the height of the turntable, which must be adjusted. The said maneuvering members for the turntable can be utilized in this respect. The computer can be arranged to identify automatically the starting point for previous scanning of the surface 2a, which requires that the position for the fixture relative to the turntable has not been altered. On the menu or form of the dental technician, there can be entered supplementary information stating that the scanning relates to an outer surface of a sleeve in question.

The invention is not limited to the embodiment shown by way of example above, but can be subject to modifications within the scope of the subsequent patent claims and the inventive concept.

We claim:

1. A method for scanning, in connection with the production of a three-dimensional dental body, an outer contour of a rotating model with a scanning device which operates at a scanning angle relative to the rotational axis of the model, said method comprising the steps of:

mounting the model in or on a rotatable holder;

supporting the model in the holder such that the contour to be scanned on the model above a preparation line is exposed to the angled scanning device;

applying the scanning device to contact a surface situated on the model below the preparation line;

activating the holder for rotation and the scanning device for contour scanning, and activating during said contour scanning at least one of the scanning device and the holder for movement in the vertical direction of the model.

2. A method according to claim 1, further including the steps of fitting the model in a fixture and adjusting the model in two mutually perpendicular directions located in the same plane, whereby centering the model relative to the rotational axis thereof.

3. A method according to claim 2 further including placing the fixture on or in the rotatable holder and centering the fixture in or on the holder using centering members.

4. A method according to claim 2, further including disposing a member in parallel with the rotational axis of the model and so as to interact with the model surface material at the preparation line, after the model has assumed its position in a fixture, whereby the scanned contour is placed between the member and the rotational axis of the model and exposed to the scanning member throughout its scanning movement without negative recesses or scanning shadows, as viewed in the scanning direction of the scanning device.

5. A method according to claim 1, further including forming a scanning device with a scanning member having a spherical front surface probe, which is adapted to bear against a surface on the model material located below said preparation line and against said contour of the model.

6. A method according to claim 5, further including actuating the scanning member of the scanning device into contact with said surface on said model material below the preparation line upon the commencement of the scanning operation and operating said scanning member in bearing contact against the contour of the model during the scanning operation until the scanning member is brought into interaction with the upper part of the model, whereupon the scanning member is controlled to cease its interaction with the model contour.

7. A method according to claim 1, further including activating and effecting vertical movement of the rotatable holder, during the scanning by the scanning member and further effecting, once the scanning member has completed its scanning of the contour of the model, a return vertical movement of the holder to a starting position.

8. A method according to claim 1, further including imputing data during the scanning of the contour of the model by the scanning member into a data file of the data processor so that the data is re-created and used in a data-processing and production operations, following the scanning operation.

9. A method according to claim 1, further including the steps of scanning the outer contour of the model for establishing the inner surface of the sleeve, said inner surface corresponding to the outer contour of the model and then applying a sleeve onto the model with great accuracy and scanning the outer contour of the sleeve in a manner equivalent to that of scanning the outer contour of the model.

10. A method according to claim 9, further including bringing the front part of a scanning member of the scanning device into contact with the surface of the model situated below the preparation line at essentially the same point in the readings of the outer contours of the model and the sleeve and making any adjustment to the vertical direction of the model, if necessary, between the readings of the outer contours.

11. A scanning device used in the production of a three dimensional dental body for scanning an outer contour of a rotating model comprising a scanning member operating at a scanning angle relative to the rotation axis of the model, a holder arranged to support the model such that the contour of the model above a preparation line on the model is exposed throughout the scanning by the angled scanning member, means for adjusting the scanning member to contact a surface situated below the preparation line, means for activating rotation of the holder, means for activating the scanning member for contour reading, and means for effecting reciprocal vertical displacement movement between the scanning member and the holder.

12. A device according to claim 11, further including means for activating the scanning device into contact with the contour of the model upon the commencement of the scanning and for performing a return movement when the scanning device has completed the contour reading, and wherein at least one of the scanning member and the holder are adapted to perform a return movement when said contour scanning is completed.

13. A device according to claim 11, wherein the model is configured with a clearly marked preparing line below which there is configured an indentation having a height of no less than about one millimeter in the vertical direction of the model, and a depth of no more than about half a millimeter.

14. A device according to claim 11, further including a fixture arranged to support the model such that it rotates around a rotational axis without substantial wobbling, and wherein the fixture is configured with manually operated adjusting members for the alignment of the model thereon.

* * * * *

UNITED STATES PATENT AND TRADEMARK OFFICE
CERTIFICATE OF CORRECTION

PATENT NO. :  5,607,305
DATED      :  March 4, 1997
INVENTOR(S):  Andersson et al.

It is certified that error appears in the above-identified patent and that said Letters Patent is hereby corrected as shown below:

Title page, Item [73],

Assignee: Nobelpharma AB
         Goteborg, Sweden

Signed and Sealed this

Twenty-ninth Day of December, 1998

Attest:

BRUCE LEHMAN

Attesting Officer

Commissioner of Patents and Trademarks